United States Patent
Bito et al.

(10) Patent No.: US 11,152,083 B2
(45) Date of Patent: Oct. 19, 2021

(54) SIMULATION METHOD FOR POLYMER MATERIAL

(71) Applicant: Sumitomo Rubber Industries, Ltd., Kobe (JP)

(72) Inventors: Yasumasa Bito, Kobe (JP); Yasuhisa Minagawa, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 960 days.

(21) Appl. No.: 15/682,089

(22) Filed: Aug. 21, 2017

(65) Prior Publication Data

US 2018/0052979 A1 Feb. 22, 2018

(30) Foreign Application Priority Data

Aug. 22, 2016 (JP) .............................. JP2016-161951

(51) Int. Cl.
*G16C 10/00* (2019.01)
*G16C 20/10* (2019.01)
*G16C 60/00* (2019.01)

(52) U.S. Cl.
CPC ............. *G16C 10/00* (2019.02); *G16C 20/10* (2019.02); *G16C 60/00* (2019.02)

(58) Field of Classification Search
CPC .................................................... G16C 10/00
See application file for complete search history.

(56) References Cited

U.S. PATENT DOCUMENTS

| | | | | |
|---|---|---|---|---|
| 2013/0245964 A1* | 9/2013 | Ueno | ..................... | G16C 99/00 702/27 |
| 2015/0142398 A1* | 5/2015 | Miller, III | .............. | G16C 10/00 703/2 |

FOREIGN PATENT DOCUMENTS

JP 2013-195220 A 9/2013

OTHER PUBLICATIONS

Bose et al., "Mathematical modelling and computer simulation of linear polymer degradation: Simple scissions," Macromolecular Theory and Simulations, vol. 13, 2004, pp. 453-473, XP55460793A.

(Continued)

*Primary Examiner* — John E Breene
*Assistant Examiner* — Jeffrey C Morgan
(74) *Attorney, Agent, or Firm* — Birch, Stewart, Kolasch & Birch, LLP

(57) ABSTRACT

A simulation method for analyzing a breakage of a molecular chain of a polymer material using a computer comprises: defining a polymeric material model by setting a molecular chain model in a virtual space corresponding to a portion of the polymeric material; and calculating a breaking of the molecular chain model. The calculating of the breaking comprises: a step S46 of performing a molecular mechanics calculation using the polymeric material model; a step S48 of performing a quantum mechanics calculation targeting on only a subset model including a particle model couple whose distance is greater than a predetermined first distance; and a step S54 of dissociating the bond between the particle models in the molecular chain model which particle models correspond to the particle model couple, if the distance between the particle models is larger than a second distance, wherein the second distance is larger than the first distance and equal to a distance between the particle models at an inflection point of a bond-dissociation potential plus a value of from 1.0 to 2.5 angstrom.

6 Claims, 15 Drawing Sheets

(56) References Cited

OTHER PUBLICATIONS

Extended European Search Report for Application No. 17186491.1, dated Apr. 4, 2018.
Kedziora et al., "Bond breaking in stretched molecules: multi-reference methods versus density functional theory," Theoretical Chemistry Accounts, vol. 135, No. 79, 2016 (Published online Mar. 2, 2016), pp. 1-16, XP35867440A.
Li et al., "Glycosidic-bond hydrolysis mechanism catalyzed by cellulase Cel7A from Trichoderma reesei: a comprehensive theoretical study by performing MD, QM, and QM/MM calculations," The Journal of Physical Chemistry B, vol. 114, No. 46, 2010 (Published on Web Oct. 28, 2010), pp. 15261-15268, XP55461781A.
Murray et al., "Analysis of diatomic bond dissociation and formation in terms of the reaction force and the position-dependent reaction force constant," Journal of Molecular Modeling, vol. 15, 2009 (Published online Dec. 4, 2008), pp. 701-706, XP19724175A.
Senn et al., "QM/MM methods for biomolecular systems," Angewandte Chemie International Edition, vol. 48, 2009, pp. 1198-1229, XP55460818A.
Van Der Kamp et al., "Combined quantum mechanics/molecular mechanics (QM/MM) methods in computational enzymology," Biochemistry, vol. 52, Apr. 4, 2013, pp. 2708-2728, XP55460817A.

\* cited by examiner

SIMULATION METHOD FOR POLYMER MATERIAL

TECHNICAL FIELD

The present invention relates to a computer simulation method for a polymer material useful for analyzing the polymer material.

BACKGROUND ART

Japanese Patent Application Publication No. 2013-195220 discloses a computer simulation method for evaluating properties of a polymeric material in order to develop polymer materials such as rubber.
In this simulation method, first, a polymeric material model is defined in the computer by arranging a molecular chain model including a plurality of particle models within a cell which is a virtual space corresponding to a portion of the polymeric material. Between the particle models of the polymeric material model, there is defined a potential which is a function of the distance between the particle models. Then, a relaxation calculation of the polymeric material model is performed based on molecular dynamics within the virtual space.
Then, using such polymeric material model, a deformation calculation is carried in order to analyze characteristics and performances of the polymer material.

SUMMARY OF THE INVENTION

Problems to be Solved by the Invention

In the actual polymeric materials, the molecular chains are broken if a larger force is applied thereto.
In the above-mentioned computer simulation method, however, a method of breaking a molecular chain model is not yet well established. Thus, there is a demand for a method in which the breakage of such a molecular chain model can be stably computed.
The present invention was made in view of the circumstances described above, and a primary object of the present invention is to provide a computer simulation method for a polymer material in which the breakage of a molecular chain model can be stably computed.
According to the present invention, a simulation method for analyzing a breakage of a molecular chain of a polymer material using a computer, comprises:
a step of defining in the computer a molecular chain model of the molecular chain comprising particle models and bond models bonding between the particle models,
a step of defining in the computer a cell which is a virtual space corresponding to a portion of the polymeric material,
a step of defining a polymeric material model by setting at least one molecular chain model in the cell,
a breaking calculation step of calculating a breaking of the molecular chain model with the computer based on a predetermined condition,
wherein the breaking calculation step comprises:
a step of defining molecular models each comprising a pair of particle models and a bond model bonding therebetween which are selected from the molecular chain model,
a step of obtaining a bond-dissociation potential by performing a quantum mechanics calculation using the molecular models and obtaining an inflection point of the bond-dissociation potential at which an energy increment becomes smaller,
a first molecular mechanics calculation step of performing a molecular mechanics calculation using the polymeric material model,
a step of determining whether or not a particle model couple exists in the molecular chain model after the first molecular mechanics calculation step, the particle model couple being a pair of the particle models bonded through the bond model whose distance is greater than a predetermined first distance,
a quantum mechanics calculation step in which, if the particle model couple exists, a quantum mechanics calculation is performed targeting on a subset model including only the particle model couple, and
a breaking step of dissociating the bond between the particle models in the molecular chain model which particle models correspond to the particle model couple, if the distance between the particle models in the subset model after the quantum mechanics calculation step, is larger than a second distance, the second distance being larger than the first distance and equal to a distance between the particle models at the inflection point plus a value of from 1.0 to 2.5 angstrom.
Preferably, the first distance is smaller than a distance between the particle models at the inflection point.
Preferably, the breaking calculation step further comprises a second molecular mechanics calculation step of performing a molecular mechanics calculation targeting on the subset model including only the particle model couple.
Preferably, the breaking calculation step comprises:
a step of calculating physical quantities including an energy Et of the polymeric material model and a force Ft acting on the polymeric material model based on calculation results of the first molecular mechanics calculation step, the second molecular mechanics calculation step and the quantum mechanics calculation step; and
a step of updating coordinates of the particle models based on the physical quantities, and
in the breaking step, based on the distance between the particle models calculated from the coordinate values, the bond between the particle models is dissociated.
The energy Et is calculated by the following expression $Et=Ea-Eb+Ec$, wherein
Ea: an energy of the polymeric material model obtained through the first molecular mechanics calculation step,
Eb: an energy of the subset model obtained through the second molecular mechanics calculation step, and
Ec: an energy of the subset model obtained through the quantum mechanics calculation step.
The force Ft is calculated by the following expression $Ft=Fa-Fb+Fc$, wherein
Fa: a force acting on the polymeric material model obtained through the first molecular mechanics calculation step,
Fb: a force acting on the subset model obtained through the second molecular mechanics calculation step, and
Fc: a force acting on the subset model obtained through the quantum mechanics calculation step.

BRIEF DESCRIPTION OF THE DRAWINGS

FIG. 15(*b*) is a diagram showing the part of the molecular chain model after the occurrence of the bond-dissociation between the particle models.

DESCRIPTION OF THE PREFERRED EMBODIMENTS

An embodiment of the present invention will now be described in detail in conjunction with accompanying drawings.

The computer simulation method for a polymeric material according to the present invention comprises a method for analyzing the breakage or scission of molecular chains of the polymer material using a computer.

Figure 1:
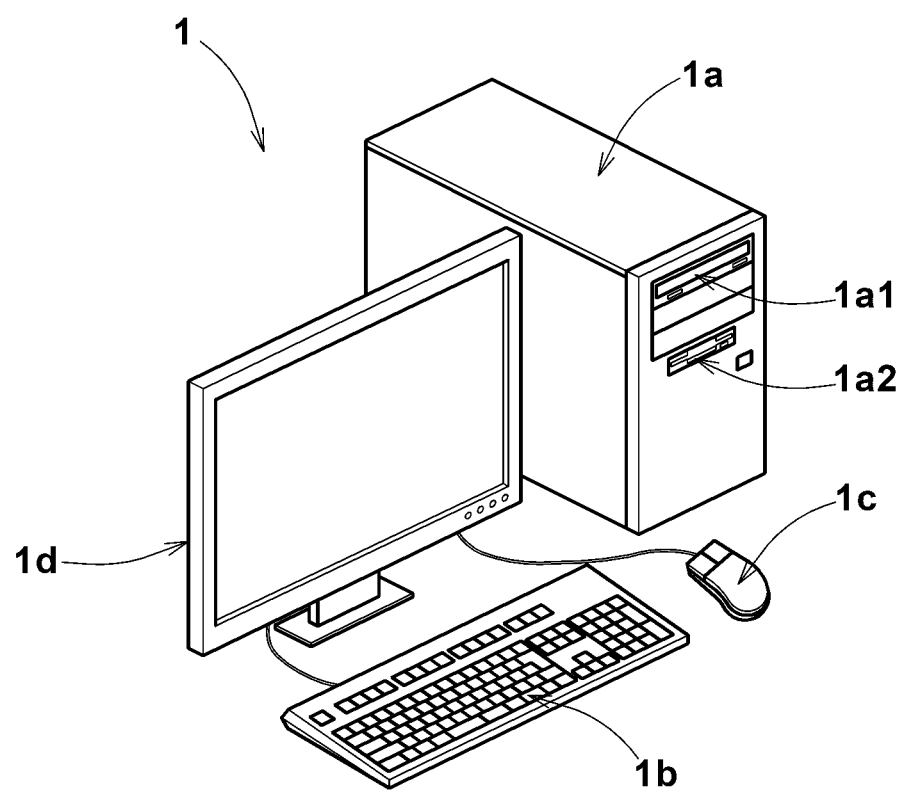
FIG. 1 is a perspective view of a computer implementing the computer simulation method for a polymer material according to the present invention.

FIG. 1 is a perspective view showing a computer implementing the simulation method according to the present invention. The computer 1 comprises a main body 1*a*, a keyboard 1*b*, a mouse 1*c*, and a display device 1*d*. The main body 1*a* includes a processing unit (CPU), ROM, a working memory, a storage device such as a magnetic disk, and disk drive devices 1*a*1, 1*a*2. In the storage device, the processing procedure (program) for executing the simulation method in the present embodiment is stored.

The polymer material includes rubber, resin, elastomer and the like.

Figure 2:
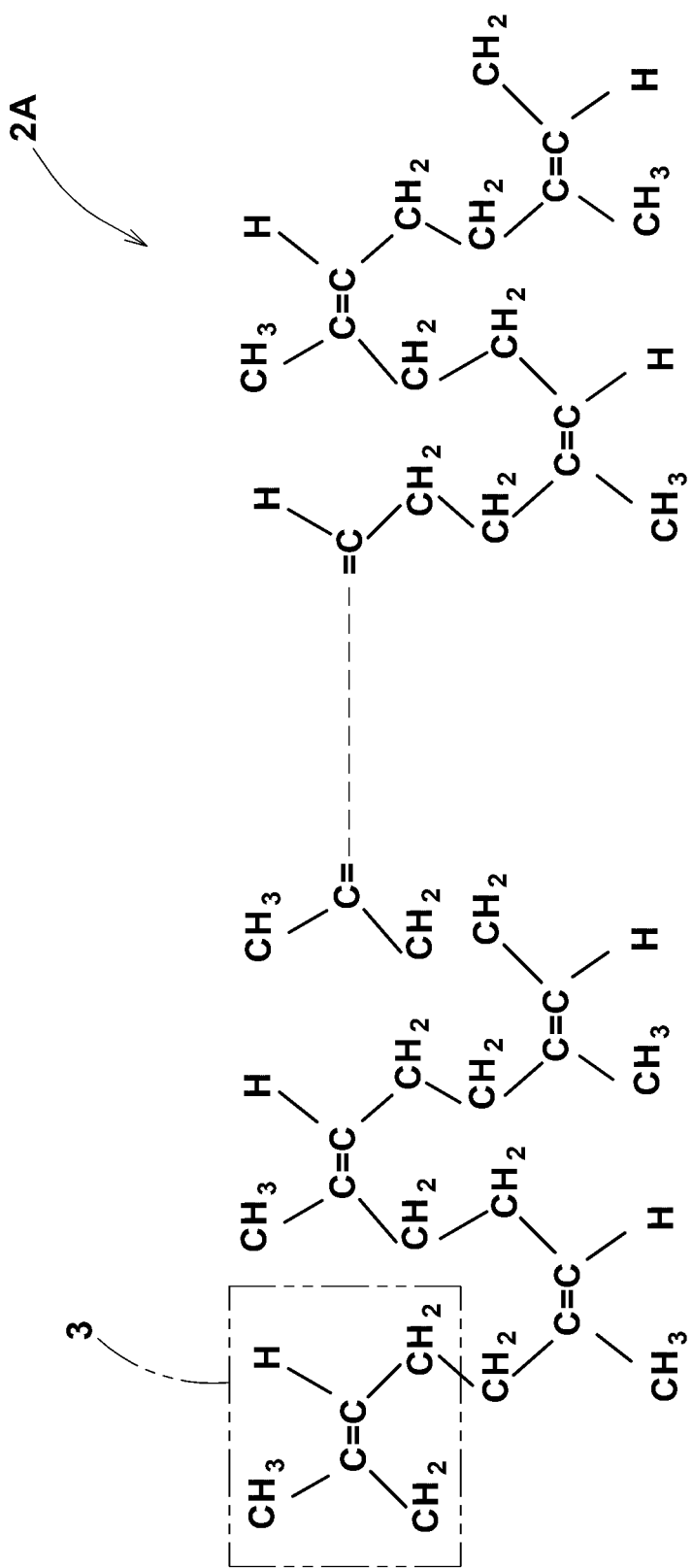
FIG. 2 shows a structural expression of polyisoprene.

The polymer material used to explain the present embodiment is cis-1,4-polyisoprene whose structural expression is shown in FIG. 2 (hereinafter, simply referred to as the "polyisoprene"). Needless to say, other polymer materials than polyisoprene can be used.

The molecular chain 2A constituting the polyisoprene is composed of monomers 3 of isoprene (isoprene molecules 3) composed of a methine group (e.g., —CH═, >C═), a methylene group (—CH2-) and a methyl group (—CH3) which are connected with n (positive integer) degrees of polymerization.

Figure 3:
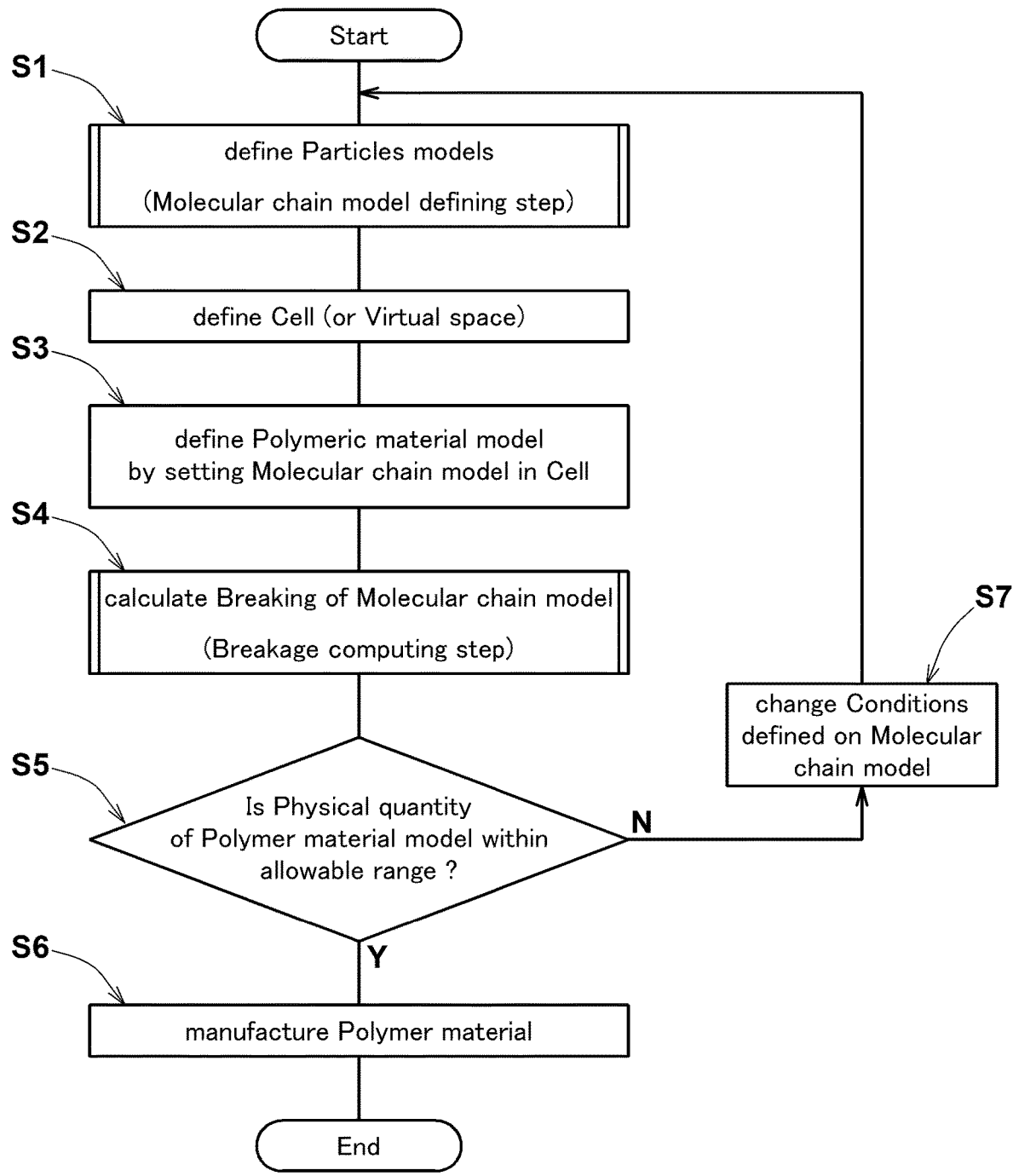
FIG. 3 is a flowchart of the computer simulation method as an embodiment of the present invention.

FIG. 3 is a flowchart of the simulation method in the present embodiment.

In the simulation method in the present embodiment, first, a molecular chain model of the molecular chain 2A is defined in the computer 1 (molecular chain model defining step S1).

Figure 4:
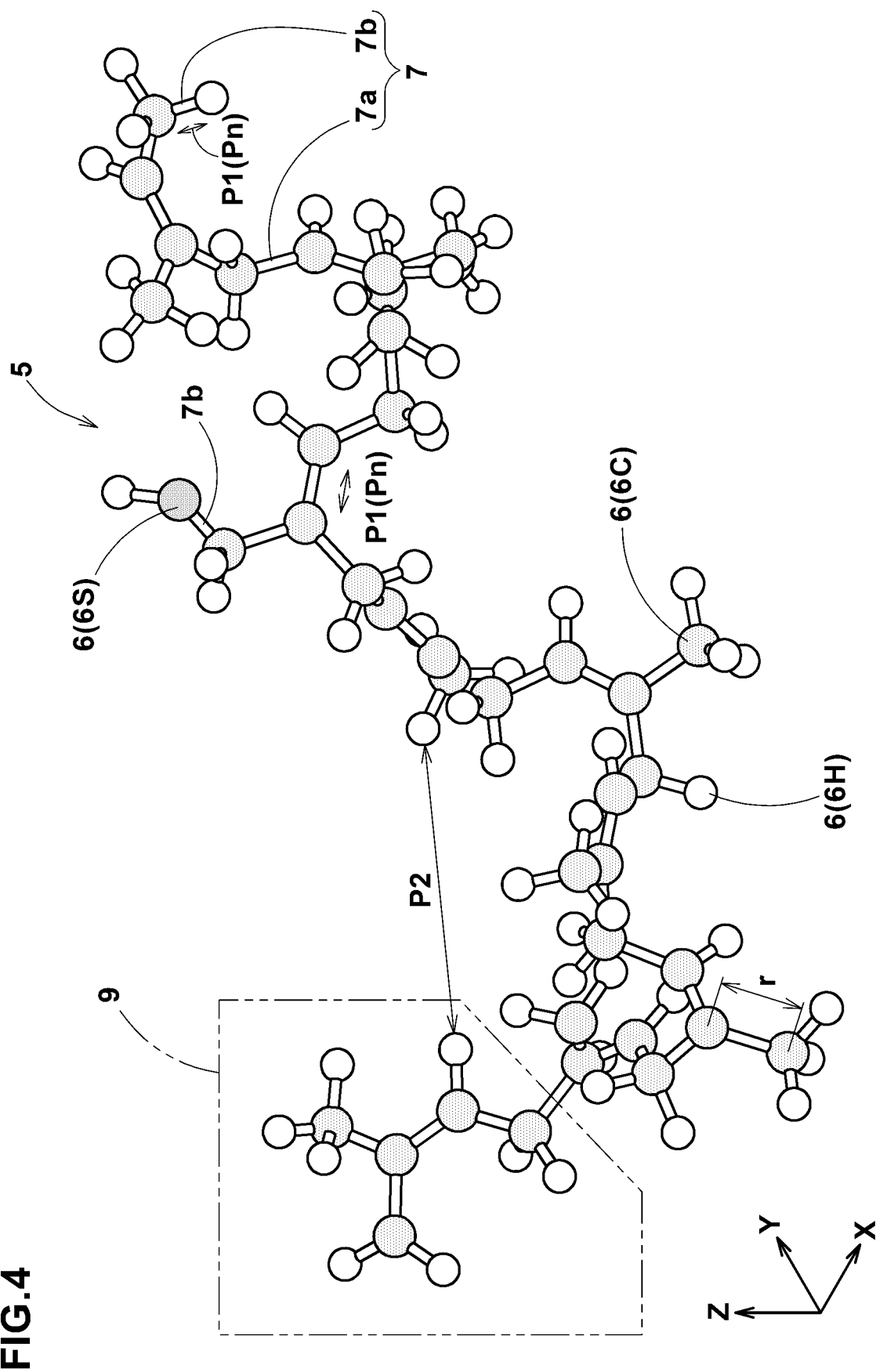
FIG. 4 is a diagram showing an example of a molecular chain model.

FIG. 4 is a diagram for conceptually showing an example of the molecular chain model 5.

The molecular chain model 5 is composed of particle models 6, and bond models 7 for bonding between the particle models 6.

In the present embodiment, the molecular chain model 5 is a full atom model. Accordingly, the particle models 6 represent the respective atoms.

In this example, the molecular chains model 5 represents polyisoprene to which one sulfur atom is cross-linked.

Based on the structure of each monomer 3 of the molecular chain 2A as shown in FIG. 2, the particle models 6 are connected by the bond models 7. Accordingly, monomers models 9 are defined.

Based on a molecular weight Mn (degrees of polymerization), the monomers models 9 are connected. Accordingly, a molecular chain model 5 is defined.

Figure 5:
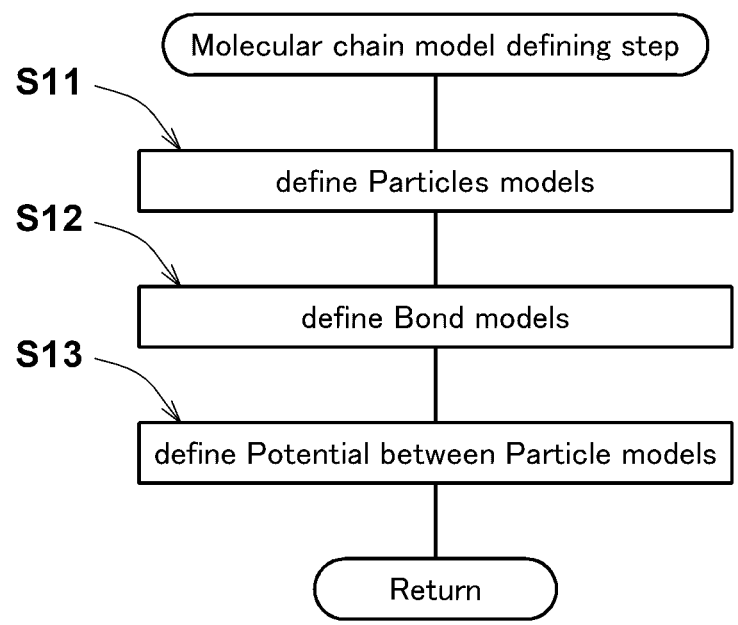
FIG. 5 is a flow chart of an example of the molecular chain model defining step S1.

FIG. 5 is a flow chart of the molecular chain model defining step S1.

In the molecular chain model defining step S1, first, the particles models 6 are defined and stored in the a computer 1, wherein, for each particle model 6, parameters such as the mass, diameter, charge, initial coordinates are defined (step S11).

In the present embodiment, the particle models 6 include a carbon particle model 6C, a hydrogen particle model 6H and a sulfur particle model 6S respectively representing a carbon atom, a hydrogen atom and a sulfur atom of the molecular chain 2A.

In the after-mentioned simulation performed based on a molecular dynamics calculation, a molecular mechanics calculation, and a quantum mechanics calculation, each particle model 6 is treated as a material point of the motion equations.

In the molecular chain model defining step S1, the bond models 7 are defined and stored in the computer 1 (step S12). The bond model 7 is to restrain between the two concerned particle models 6. In the present embodiment, the bond models 7 include that for a main chain 7*a* and that for a side chain 7*b*. The main chain 7*a* is for bonding between the carbon particle models 6C. The side chain 7*b* includes that bonding between the carbon particle model 6C and the hydrogen particle model 6H, and that bonding between the carbon particle model 6C and the sulfur particle model 6S.

In the molecular chain model defining step S1, a potential causing an interaction (including a repulsive interaction and an attractive interaction) is defined between the particle models 6 (Step S13).

The potential includes a first potential P1 defined between every two of the particle models 6 bonded through one of the bond models 7, and a second potential P2 defined between the particle models 6 not bonded through the bond models 7 as shown in FIG. 4.

Figure 6A:
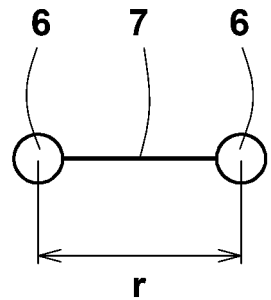
FIGS. 6(*a*)-6(*c*) are diagrams each showing a portion of the molecular chain model for explaining a first potential P1.
Figure 6B:
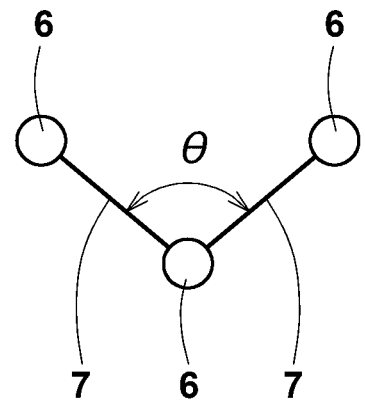
Figure 6C:
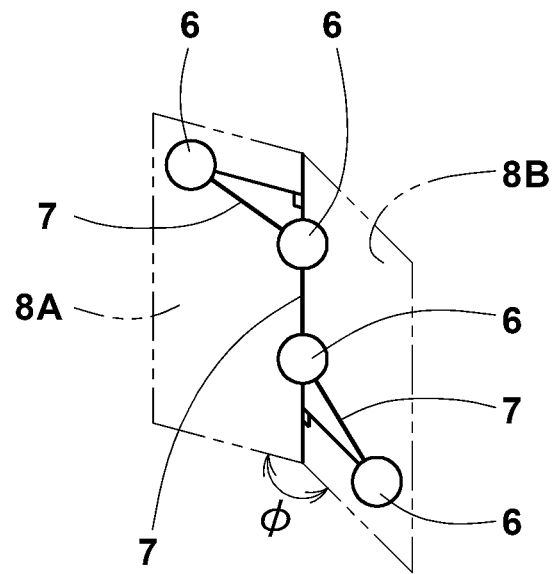

FIGS. 6(*a*)-6(*c*) are diagrams each showing a portion of the molecular chain model 5 for explaining the first potential P1.

On the molecular chain model 5, a bond distance r (bond length) between the bonded particle models 6 as shown in 6(*a*), and a bond angle θ formed by the three particles models 6 bonded through two bond models 7 as shown in 6(*b*), are defined. Further, as shown in FIG. 6(*c*), a dihedral angle φ defined between a plane 8A formed by a set of three consecutive particle model 6 and a plane 8B formed by another set of three consecutive particle model 6 in the four particle models 6 bonded through three bond models 7, is defined. The bond distance r, the bond angle θ and the dihedral angle φ are changed by external and internal forces acting on the molecular chain model 5.

The bond distance r, the bond angle θ and the dihedral angle φ are respectively defined by a bond potential $u_{bond}(r)$ defined by the following expression (1), a bond angle potential $U_{angle}(\theta)$ defined by the following expression (2) and a dihedral angle potential $u_{torsion}(\phi)$ defined by the following expression (3)

$$U_{bond}(r) = \frac{1}{2}k_1(r-r_0)^2 \quad (1)$$

$$U_{angle}(\theta) = \frac{1}{2}k_2(\theta-\theta_0)^2 \quad (2)$$

$$U_{torsion}(\phi) = k_3 \sum_{n=0}^{N-1} A_n \cos^n \phi \quad (3)$$

wherein
r: the bond distance,
$r_0$: equilibrium distance (equilibrium length),
k1, k2: spring constants,
θ: the bond angle,
$\theta_0$: equilibrium angle,
k3: intensity of the dihedral angle potential
N−1: degree of a polynomial of the dihedral angle potential,
φ: the dihedral angle,
An: dihedral angle constant.
Incidentally, the bond distance r and the equilibrium distance $r_0$ are distances between the centers (not shown) of the particle models 6.

The values of the constants of the bond potential $u_{bond}(r)$, and bond angle $u_{angle}(\theta)$, and the binding dihedral angle potential $u_{torsion}(\phi)$ can be set as appropriate, preferably, based on the paper (J. Phys. Chem. 94, 94, 8897(1990)) in accordance with the structure of the molecule chains Mc.

In the present embodiment, the second potential P2 defined between the particle models 6 not bonded through the bond model 7 is a Lennard-Jones (LJ) potential $u_{LJ}(r_{ij})$ defined by the following expression (4).

$$U_{LJ}(r_{ij}) = 4\varepsilon\left[\left(\frac{\sigma}{r_{ij}}\right)^{12} - \left(\frac{\sigma}{r_{ij}}\right)^6\right] \quad (4)$$

wherein
$r_{ij}$: distance between the centers of the particle models,
∈: intensity of the LJ potential defined between the particle models,
σ: corresponding to the diameter of the particle model.

According to the distance $r_{ij}$ between the particle models, the second potential P2 causes repulsive and attractive forces as follows.

When the distance $r_{ij}$ is smaller than the σ, the second potential P2 causes a repulsive force between the particle models 6, which increases as the distance $r_{ij}$ is decreased. When the distance $r_{ij}$ becomes equal to the σ, the second potential P2 becomes its minimum, and neither the repulsive force nor the attractive force is caused between the particle models 6.

When the distance $r_{ij}$ is larger than the σ, the second potential P2 causes an attractive force between the particle models 6.

In the present embodiment,
between the sulfur particle models 6S,
between the carbon particle models 6C,
between the carbon particle model 6C and the hydrogen particle model 6H,
between the sulfur particle model 6S and the carbon particle model 6C, and
between the sulfur particle model 6S and the hydrogen particle model 6H,
different second potentials P2 are respectively defined.
Here, the different second potentials P2 mean that the constant in the equation (4) is different.
The constant can be appropriately defined, for example, based on the paper (J. Phys. Chem. 94, 94, 8897(1990)).

In the simulation method in the present embodiment, a cell 17 which is a virtual space corresponding to a portion of the polymeric material is defined in the computer 1 (step S2).

The cell 17 is used to define the polymeric material model 16 by arranging the molecular chain model 5 therein.

Figure 7:
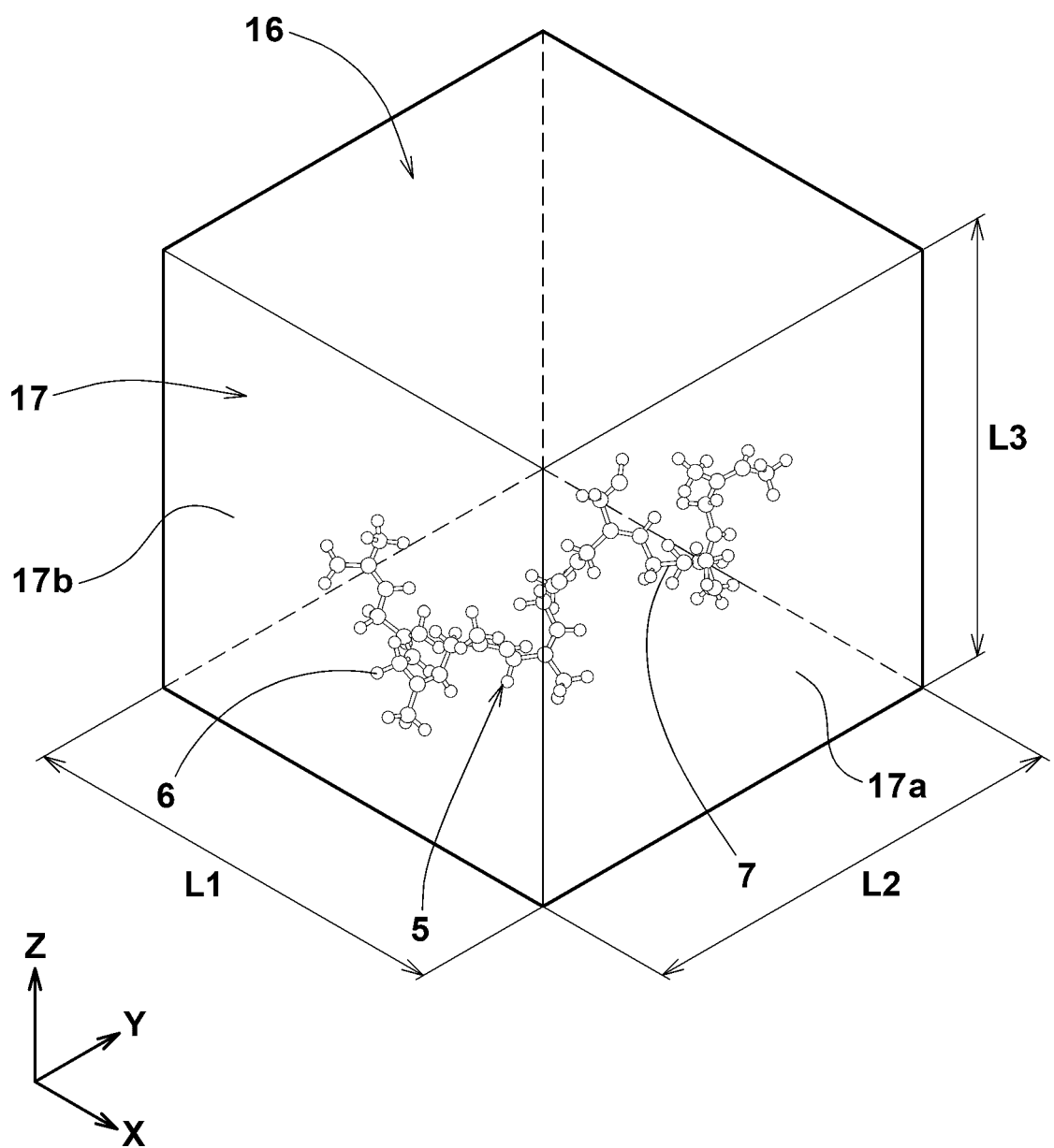
FIG. 7 is a conceptual diagram showing an example a polymeric material model.

FIG. 7 is a conceptual diagram showing an example of the polymeric material model 16. In this example, the cell 17 is a rectangular parallelepiped having three pairs of opposite flat surfaces 17a and 17b.

On each of the surfaces 17a and 17b, a periodic boundary condition is defined. Thus, it is possible to treat the cell 17 such that one surface 17a is continuous (connected) with the other surface 17b. In such cell 17, therefore, it is possible to compute a portion of the molecular chain model 5 moving out of the cell 17 through one plane 17a as being moving into the cell 17 through the other opposite plane 17b.

The lengths L1, L2 and L3 of the sides of the cell 17 may be arbitrarily defined. But, one of them, for example, the length L1 is preferably set to be more than 2 times the radius of inertia of the molecular chain model 5. Thereby, during the molecular dynamics calculation performed on the inside of the cell 17, the molecular chain model 5 is hard to collide with a self-image generated by the periodic boundary condition. Therefore, it is possible to stably compute the spatial spread of the molecular chain model 5. In order to define at least a portion of the volume of the polymeric material, a volume which is stable under 1 atmospheric pressure is defined on the cell 17.

The data defining the cell 17 are stored in the computer 1.

In the simulation method in the present embodiment, the polymeric material model 16 is defined in the computer 1 (step S3).

The polymeric material model 16 is defined by setting at least one molecular chain model 5 within the cell 17 on the computer 1. The number of the molecular chain model 5 set within the cell 17 can be set as appropriate. But, preferably, the number is 30 or more.

Then, a relaxation calculation of the cell 17 in which the molecular chain models 5 are set, is performed by making a molecular dynamics (MD) calculation. Thereby, the polymeric material model 16 in which the molecular chain models 5 are relaxed, is defined.

In the molecular dynamics calculation in the present embodiment, the Newton's equation of motion is applied to the cell 17 on the assumption that the molecular chain models 5 conform to the classical mechanics for a given time period. During the molecular dynamics calculation, the motion of each particle model 6 is tracked by obtaining its position every unit timestep.

The molecular dynamics calculation (relaxation calculation) can be made by the use of, for example, COGNAC (Molecular dynamics simulation system) included in J-OCTA (Integrated simulation system) created by JSOL Corporation.

During the molecular dynamics calculation (relaxation calculation), in the cell 17, the pressure and temperature, or the volume and temperature are kept constant.
The molecular dynamics calculation is continued until the artificial initial arrangement of the molecular chain models 5 can be regarded as being fully eliminated.
In the step S3, therefore, the molecular chain models 5 can be relaxed accurately, approximating the actual molecular motion of the polymer material.

Through such relaxation calculations, the polymeric material model 16 is defined, and stored in the computer 1.

Then, in the simulation method in the present embodiment, on the basis of a predetermined condition, breakage of the molecular chain models 5 is computed by the computer 1 (breakage computing step S4).
In the breaking calculation step S4 in the present embodiment, an elongation simulation to elongate the polymeric material model 16 in one axis direction (for example, z-axis direction shown in FIG. 7) is performed.

In the elongation simulation in the present embodiment, using a molecular mechanics (MM) calculation and a quantum mechanics (QM) calculation, the elongation of the polymeric material model 16 is calculated every unit timestep until the polymeric material model 16 is elongated to a predetermined length (upper limit value).

In the elongated polymer material model 16, therefore, the distances between the particle models 6 of the molecular chain model 5 are increased. The state of the molecular chain model 5 which is broken by the increase in the distance between the particle models 6 is calculated.

The molecular mechanics calculation can be made using the above-mentioned software used in the molecular dynamics calculation.

Further, the quantum mechanics calculation is performed on the assumption that the molecular chain models 5 conform to interactions based on the nuclei and electrons. For each of the particle models 6, the state and motion of each electron are tracked every unit timestep.
The quantum mechanics calculation can be made by the use of Gaussian 03 or Gaussian 09 (Quantum chemical calculation program) created by Gaussian, Inc.
Incidentally, the accuracy of the quantum mechanics calculation is higher than that of the molecular mechanics calculation.

In the elongation simulation in the present embodiment, the molecular mechanics calculation is performed, targeting on the entirety of the polymeric material model 16.
Then, targeting on only part of the molecular chain model 5 in which breakage is likely to occur between the particle models 6 of the molecular chain model 5, the quantum mechanics calculation is performed in order to compute the breakage of the molecular chain model 5 in detail.
Therefore, the breaking calculation step S4 can greatly reduce the computation time as compared to the case of the quantum mechanics calculation being performed for the entirety of the polymeric material model 16.

Figure 8:
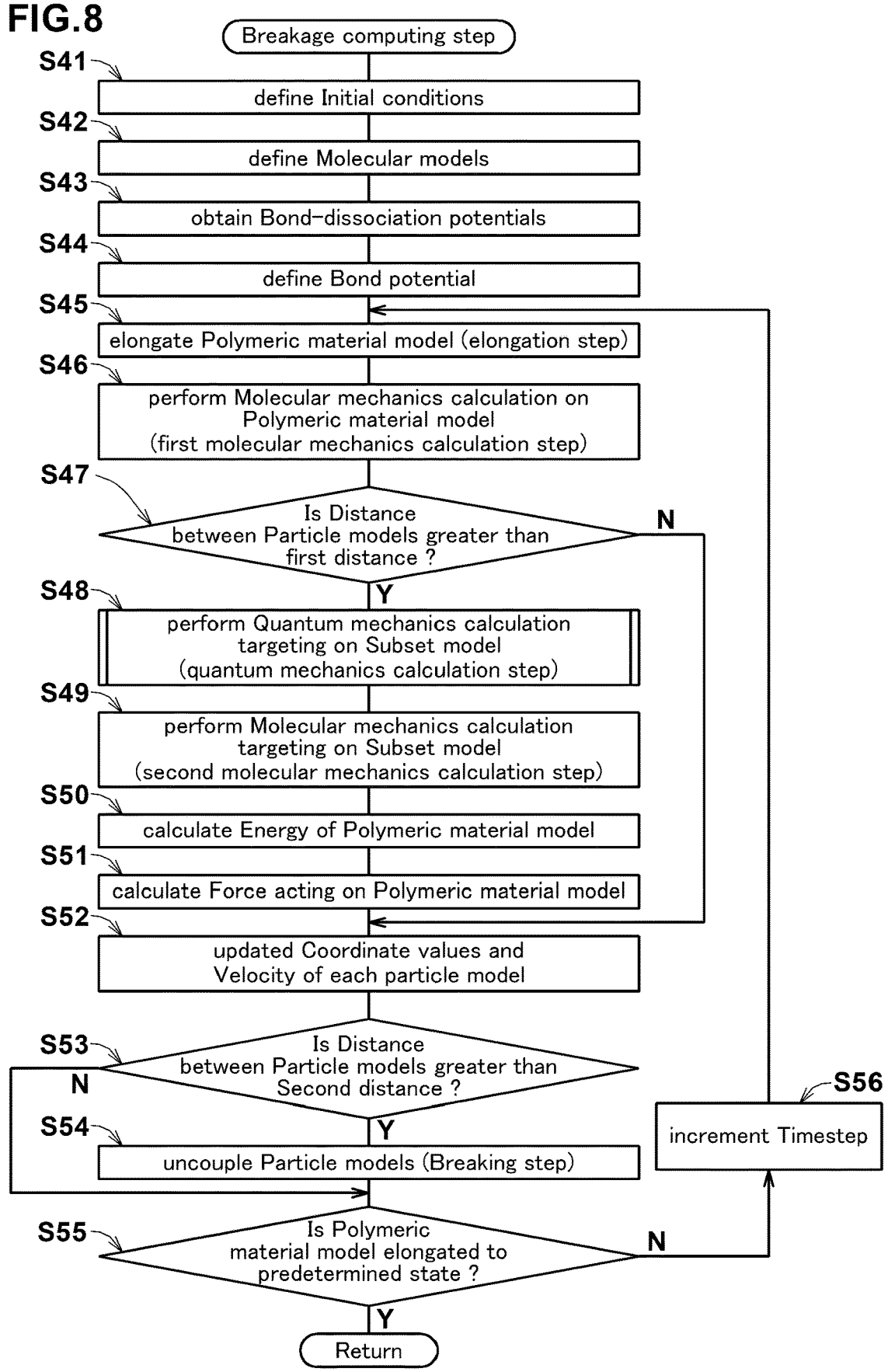
FIG. 8 shows a flowchart of an example of the breaking calculation step S4.

FIG. 8 shows a flowchart of the breaking calculation step S4.
In the step S4 in the present embodiment, first, initial conditions for carrying out the elongation simulation of the polymeric material model 16 are defined and stored in the computer 1 (Step S41).

Figure 9:
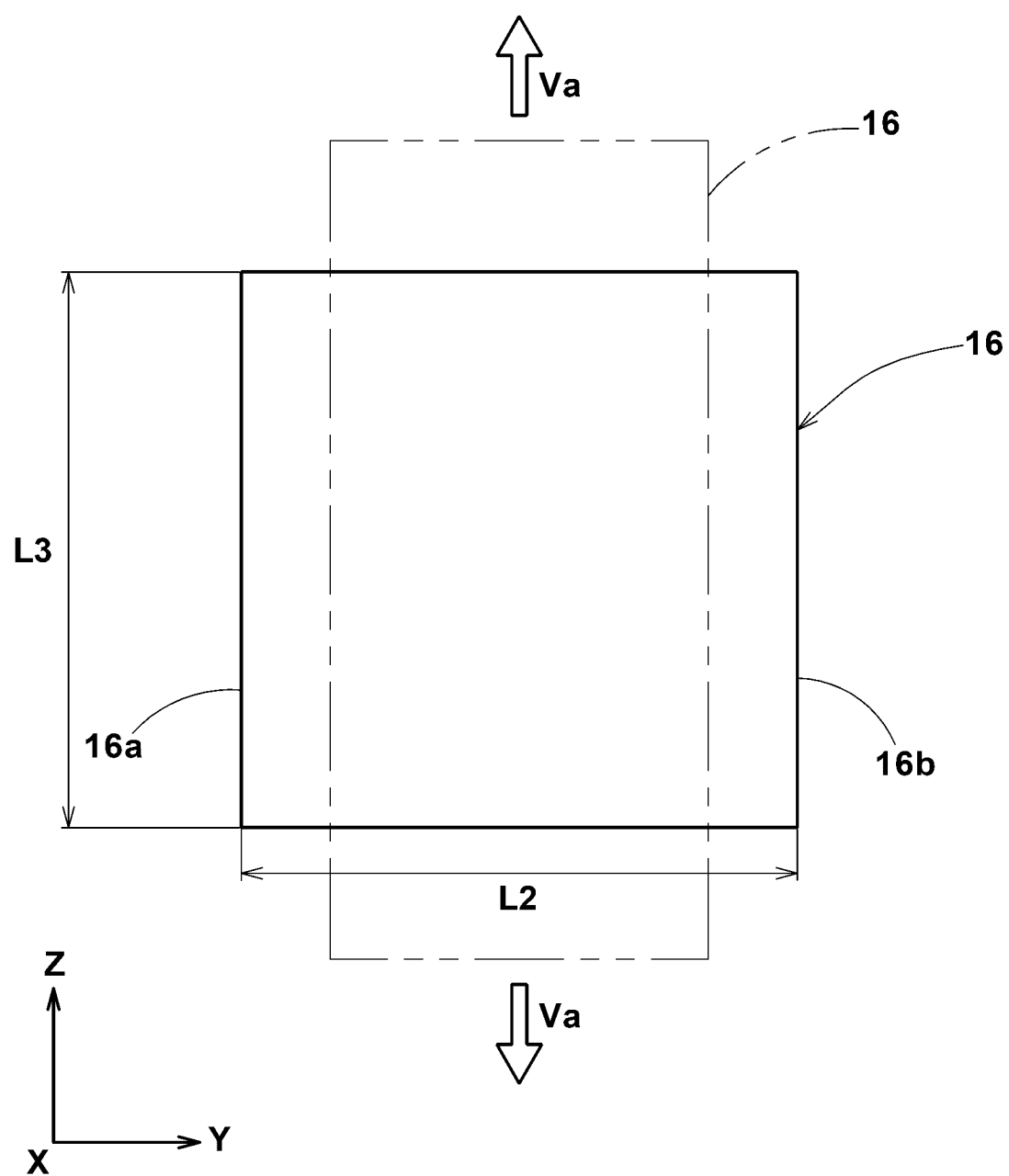
FIG. 9 is a diagram for explaining an elongation deformation simulation of the polymeric material model.

FIG. 9 is a diagram for explaining the elongation simulation of the polymeric material model 16.
Based on the Poisson's ratio of the polymer material model 16, the lengths L1, L2, L3 of the polymeric material model 16 at each of the unit timesteps are defined as the initial conditions. Thus, in the breaking calculation step S4, the elongation simulation to elongate the polymeric material model in the one axis direction (e.g. z-axis direction) is carried out based on the Poisson's ratio of the polymeric material model 16.
The elongation rate Va in the one axis direction of the polymeric material model 16 can be arbitrarily set according to the polymer material and the simulation conditions. In the present embodiment, the elongation rate va is set to a value in a range from 200 meters/sec to 300 meters/sec in order to simulate the polymer material elongated at a high velocity, for example.

In the breaking calculation step S4 in the present embodiment, molecular models 11 are defined and stored in the computer 1, wherein each of the molecular models 11 comprises two particle models 6 bonded through a bond model 7 which are of the molecular chain model 5 (step S42).

The molecular models 11 include combinations of all kinds of the particle models 6. In other words, the molecular models 11 in the present embodiment include:
a molecular model 11A comprising two sulfur particle models 6S,
a molecular model comprising two carbon particle models 6C,
a molecular model comprising a carbon particle model 6C and a hydrogen particle model 6H,
a molecular model comprising a sulfur particle model 6S and a carbon particle model 6C, and
a molecular model comprising a sulfur particle model 6S and a hydrogen particle model 6H.
The molecular models are used when obtaining the after-mentioned bond-dissociation potential.

Figure 10:
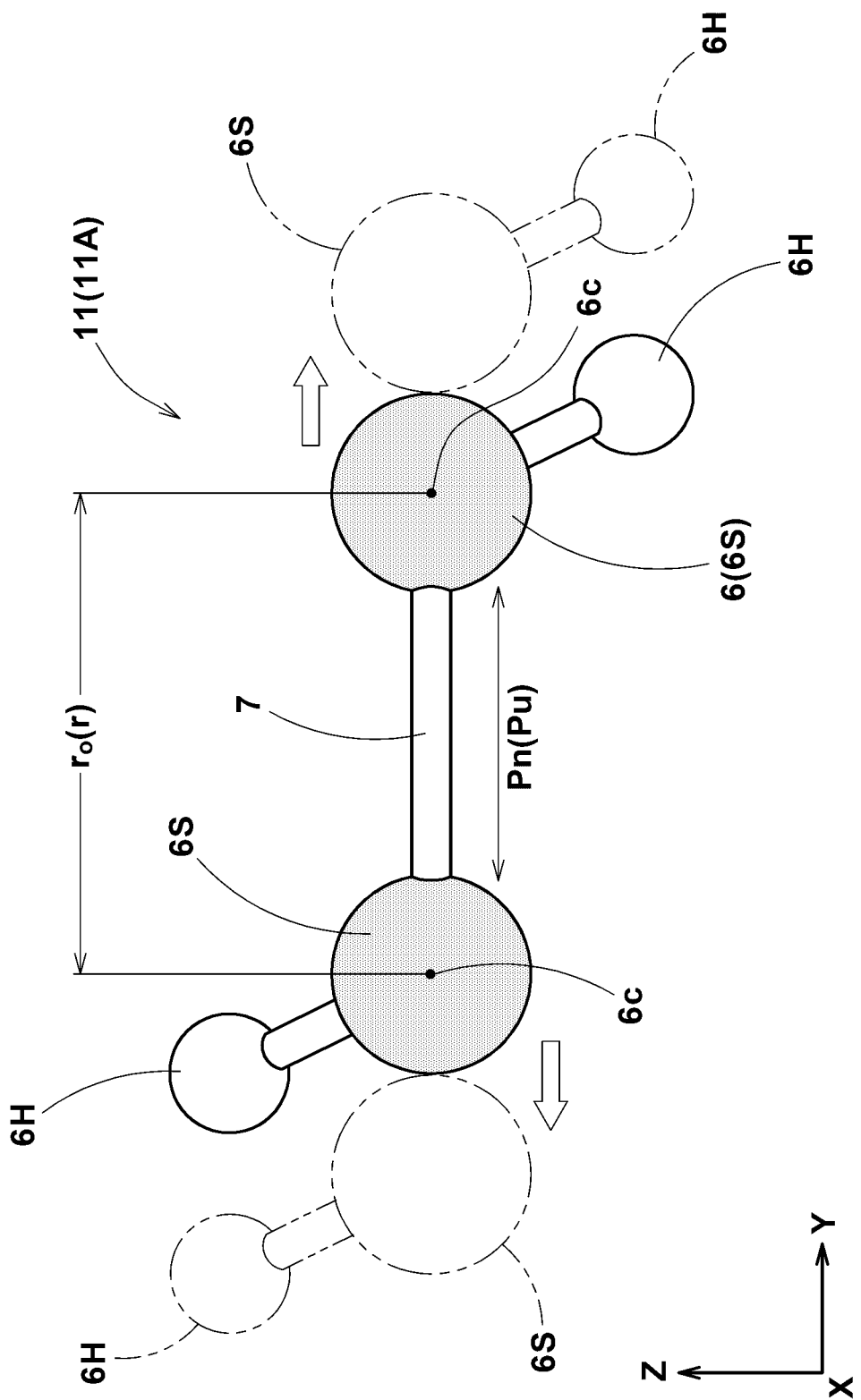
FIG. 10 is a diagram showing an example of the molecular model.

FIG. 10 shows the molecular model 11A as an example. In this example, two sulfur particle models 6S bonded through a bond model 7 are included.

In order that, during the quantum mechanics calculation, each of the molecular models 11 maintains its stable structure, each of the molecular models 11 further includes one or more additional hydrogen particle models 6H whose number corresponds to the difference between the sum of the valencies of the atoms modeled by the two particle models 6 and the sum of the bond numbers of the two particle models 6.
The additional hydrogen particle models are bonded with appropriate particle models through bond models 7.
In the molecular model 11A shown in FIG. 10, the difference between the sum (2+2) of the valencies (2) of the two sulfur atoms modeled by the two sulfur particle models 6S and the sum (1+1) of the bond numbers (1) of the two sulfur particle models 6S is 2, therefore, two additional hydrogen particle models 6H are respectively bonded with two sulfur particle models 6S through two bond models 7.

In this way, each of the molecule models 11 is defined.
In the breaking calculation step S4 in the present embodiment, based on the quantum mechanics calculation using the molecular models 11, a bond-dissociation potential having an inflection point at which the energy increment is reduced is determined (step S43).

The bond-dissociation potential Pu differs depending on the combination of the two bonded particle models 6.
In the present embodiment, therefore, based on the different molecular models 11 defined in the step S42, different bond-dissociation potentials Pu between two sulfur particle models 6S, between two carbon particle models 6C, between a carbon particle model 6C and a hydrogen particle model 6H, between a sulfur particle model 6S and a carbon particle model 6C, and between a sulfur particle model 6S and a hydrogen particle model 6H, are obtained.

In the step S43, firstly, between the two particle models 6 of each of the molecule models 11, a theory and basis function used in the quantum mechanics calculation are defined and stored in the computer 1.

As the theory, the density functional theory (functional: B3LYP) is defined in the present embodiment.

As the basis function, the basis function 6-31G(d) is defined in the present embodiment.

The theory and basis function used in the quantum mechanics calculation can be defined by using the above-mentioned quantum chemical calculation program Gaussian 03 or Gaussian 09.

In the step S43, the bond-dissociation potentials Pu between the particle models 6 are obtained through a simulation performing the quantum mechanics calculation using the molecular models 11.

In the molecular model 11, an equilibrium distance $r_0$ between the particle models 6, which is determined by the above theory and basis functions, and at which interactions caused by the nuclei and electrons balance, is defined as shown in FIG. 10.

In the step S43 in the present embodiment, from a state in which the particle models 6 abuts each other to a state in which the distance r between the particle models 6 becomes larger than the equilibrium distance $r_0$ (e.g., 4.5 angstroms), the distance r is increased by 0.1 angstrom per a unit step through the quantum mechanics calculation. Here, the equilibrium distance $r_0$ and the distance r are those between the centers 6C of the particle models 6.

Further, in the quantum mechanics calculation of the present embodiment, based on the unrestricted density functional method, the total energy of the molecular model 11 is calculated every unit step. Then, based on a relationship between the distance r between the particle models 6, and the total energy of the molecular model 11, the bond-dissociation potential Pu is obtained.

Figure 11:
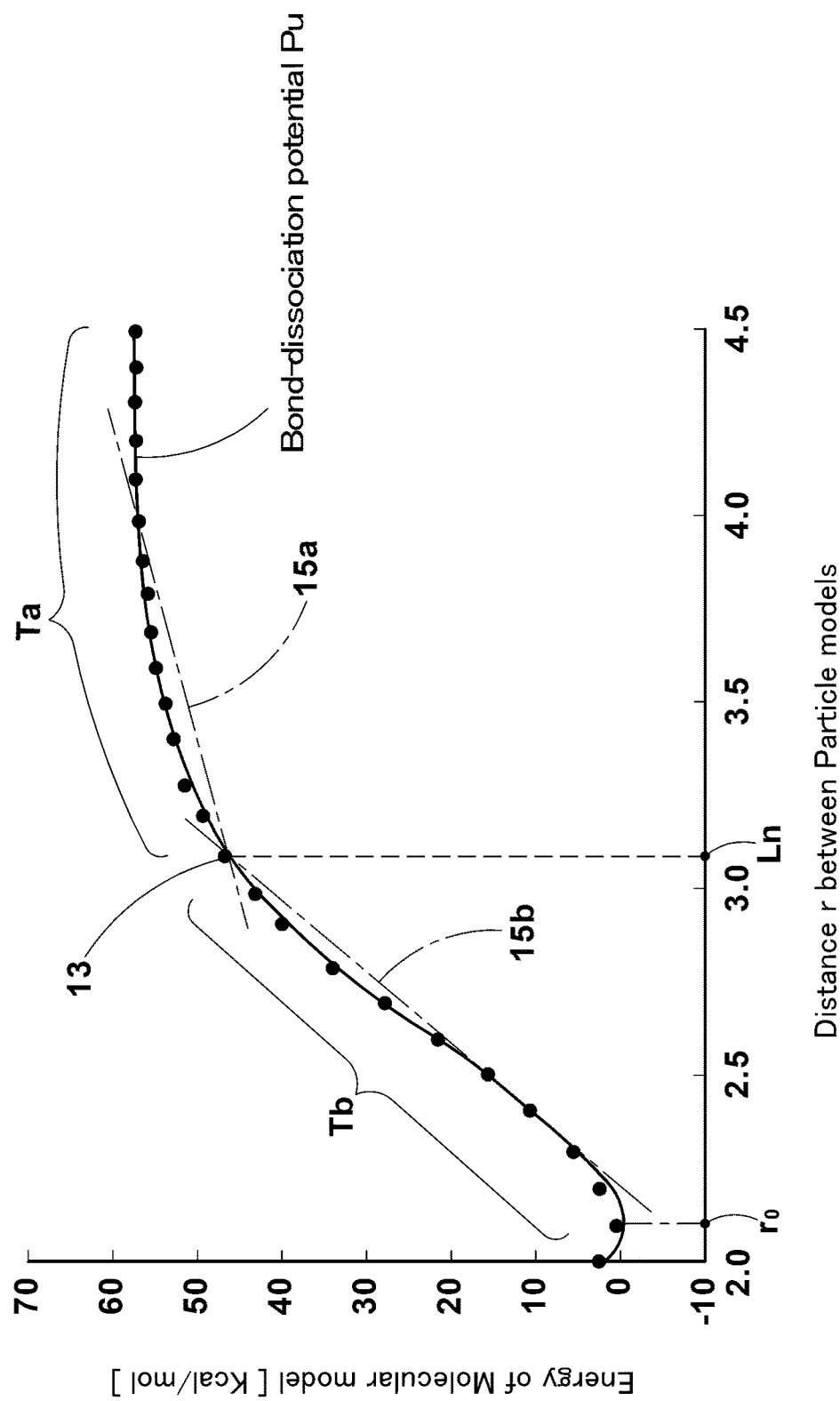
FIG. 11 is a graph showing an example of the bond-dissociation potential Pu.

FIG. 11 is a graph showing an example of the bond-dissociation potential Pu.

In this example, the total energy of the molecular model 11 (repulsion between the particle models 6) becomes larger as the distance r between the particle models 6 becomes smaller than the equilibrium distance $r_0$ (2.1 in the present embodiment) and the difference therebetween becomes increased.

When the distance r is 2.1, the total energy becomes minimum, and neither a repulsive force nor an attractive force occur between the particle models 6.

When the distance r becomes larger than the equilibrium distance $r_0$, the total energy of the molecular models 11 (attraction between the particle models 6) increases.

Thus, the bond-dissociation potential Pu can cause repulsive and attractive forces depending on the distance r.

In a range where the distance r between the particle models 6 is greater than the equilibrium distance $r_0$, the bond-dissociation potential Pu has an inflection point 13 where the increment of the total energy of the molecular model 11 is decreased than the previous one.

The increments of the total energy of the molecular model 11 are larger
in a range Tb where the distance r is smaller than that at the inflection point 13 than
in a range Ta where the distance r is larger than that at the inflection point 13.

This means that, in the range Tb, the particle models 6 are mutually bonded more firmly. On the other hand, in the range Ta, the bonded particle models 6 are partly dissociated or the bond orders are decreased. Thus, the inflection point 13 can be considered as the boundary between the bond and dissociation of the particle models 6.

In the step S43, the quantum mechanics calculation is performed, targeting on all kinds of the molecular models 11 described above, and the following bond-dissociation potentials Pu are obtained and stored in the computer 1:

the bond-dissociation potential Pu between the two sulfur particle models 6S, the bond-dissociation potential Pu between the two carbon particle models 6C, the bond-dissociation potential Pu between the carbon particle model 6C and the hydrogen particle model 6H, the bond-dissociation potential Pu between the sulfur particle model 6S and the carbon particle model 6C, and, the bond-dissociation potential Pu between the sulfur particle model 6S and the hydrogen particle model 6H.

In the breaking calculation step S4 in the present embodiment, a bond potential Pn used in the molecular mechanics calculation is defined (step S44).

The bond potential Pn is to be defined between every two of the particle models 6 bonded through the bond models 7 in the molecular chain model 5 as shown in FIG. 4.

In the present embodiment, the bond potential Pn is approximate to the bond-dissociation potential Pu.

Since the bond potential Pn is approximate to the potential in the quantum mechanics calculation, the difference between the results of the quantum mechanics calculation and the results of the molecular mechanics calculation can be minimized.

Figure 12:
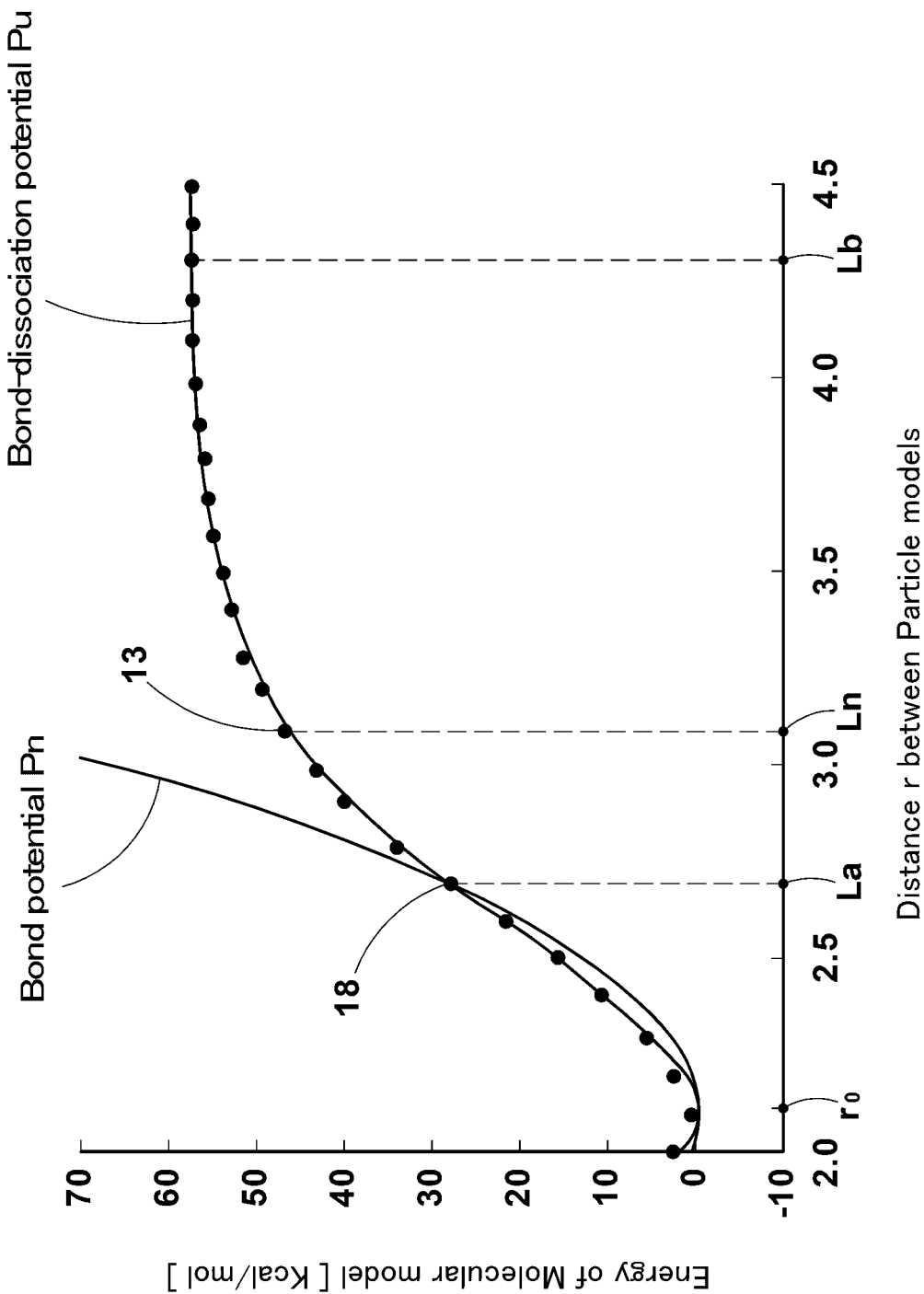
FIG. 12 is a graph showing an example of a bond potential Pn and the bond-dissociation potential Pu.

FIG. 12 is a graph showing an example of a bond-dissociation potentials Pu and a bond potential Pn.

In the step S44 of the present embodiment, a harmonic oscillator type function based on the Hooke's law is approximated to the bond-dissociation potential Pu, and thereby, the bond potential Pn is obtained.

The harmonic oscillator type function is defined by the following expression (5).

$$V = \tfrac{1}{2} k (r - r_0)^2 \qquad (5)$$

wherein
v: the energy of the molecular model,
k: a spring constant,
r: the distance between the particle models,
$r_0$: the equilibrium distance between the particle models.

The expression (5) is a quadratic function which expresses the relationship between the distance r between the particle models 6 and the energy of the molecular model.

In the present embodiment, since the bond potential Pn is obtained by approximating the harmonic oscillator type function to the bond-dissociation potential Pu in the range Tb as shown in FIG. 11, the bond potential Pn approximates to the bond-dissociation potential Pu before occurrence of a breakage between the particle models 6 or a decrease in the bond orders.

In order to approximate the harmonic oscillator type function to the bond-dissociation potential Pu, the least square method can be used. In such bond potential Pn, the complex bond-dissociation potential Pu can be expressed by the simple harmonic oscillator type function.

In the step S44, it is desirable to approximate the harmonic oscillator type function to the bond-dissociation potential Pu in a range
from the greatest lower bound of the energy of the bond-dissociation potential Pu (the energy of the molecular model 11) at the equilibrium distance $r_0$ to a point between 50% and 80% (possibly between 50% and 70%, at least between 50% and 60%) of the least upper bond of the energy.

Thereby, in the above-mentioned range Tb, it is possible to accurately approximate the bond potential Pn to the bond-dissociation potential Pu.

If the above-mentioned point is less than 50% of the least upper bond of the energy, the bond-dissociation potential Pu can not be accurately approximated by the harmonic oscillator type function. If the above-mentioned point is more than 80% of the least upper bond of the energy, it becomes necessary to approximate the harmonic oscillator type function to the bond-dissociation potential Pu in the range Tb as well as a portion of the range Ta. This is however difficult.

In the step S44, the bond potential Pn is obtained with respect to each of the bond-dissociation potential Pu between the two sulfur particle models 6S, the bond-dissociation potential Pu between the two carbon particle models 6C, the bond-dissociation potential Pu between the carbon particle model 6C and the hydrogen particle model 6H, the bond-dissociation potential Pu between the sulfur particle model 6S and the carbon particle model 6C, and, the bond-dissociation potential Pu between the sulfur particle model 6S and the hydrogen particle model 6H.

In the step S44, instead of the first potential P1, the bond potential Pn is defined between the particle models 6 bonded through the bond model 7 in the molecular chain model 5 shown in FIG. 4.

As to the particle models 6 not bonded through the bond model 7, however, the bond potential Pn is not defined, and the second potential P2 defined therebetween is maintained.

In the breaking calculation step S4 in the present embodiment, then, a deformation calculation for elongating the polymeric material model 16 is performed (elongation step S45).

In the present embodiment, based on the Poisson's ratio defined as the initial condition, the deformation (elongation) of the polymeric material model 16 is calculated.

In the elongation step S45, the polymeric material model 16 elongated in the one axis direction at the current unit timestep, is calculated.

By the elongation of the polymer material model 16, the molecular chain model 5 (shown in FIG. 7) is also elongated in the one axis direction, and at least some of the particle models 6 bonded through the bond model 7 are increased in the distance r.

In the breaking calculation step S4 in the present embodiment, then, with respect to the polymeric material model 16 deformed through the elongation step S45, a molecular mechanics (MM) calculation is carried out (first molecular mechanics calculation step S46).

In the first molecular mechanics calculation step S46, physical quantities of the polymeric material model 16 are calculated and stored in the computer 1. The physical quantities include an energy Ea of the polymeric material model 16, and a force Fa acting on the polymeric material model 16.

Then, in the breaking calculation step S4 in the present embodiment, it is judged whether or not a pair 21 of the particle models 6 bonded through the bond model 7 whose distance r is greater than a predetermined first distance La (hereinafter, the bond-dissociating particle model couple 21) exists in the molecular chain model 5 after the first molecular mechanics calculation step S46 (step S47).

Specifically, with respect to all of the molecular chain models 5 set in the cell 17, all of the particle models 6 bonded through the bond models 7 are calculated for the distance r.

However, the distances between the particle models 6 not bonded through the bond model 7 are not calculated.

Then, the molecular chain models 5 are searched for a pair of the bonded particle models 6 whose distance r is greater than the first distance La, and the found paired particle models 6 and the bond model 7 therebetween are determined as the bond-dissociating particle model couple 21.

In the present embodiment, the first distance La is set to a value smaller than the distance r(Ln) between the particle models 6 at the inflection point 13 of the bond-dissociation potential Pu as shown in FIG. 12, and the first distance La is set to be larger than the equilibrium distance $r_0$ of the concerned particle models 6.

As explained above, the inflection point 13 can be considered as the boundary between the bond and dissociation of the particle models 6. Therefore, it can be considered to be likely to dissociate the bond between the particle models 6 of the bond-dissociating particle model couple 21 wherein the distance r is greater than the first distance La.

In the step S47, therefore, it is possible to determine whether the bond-dissociating particle model couple 21 where the particle models 6 are likely to be dissociated, exists or not.

The first distance La may be arbitrarily set to values smaller than the distance r at the inflection point 13.

In the present embodiment, as shown in FIG. 12, the first distance La is set to the value of the distance r at the intersection 18 of the curve of the bond-dissociation potential Pu and the curve of the bond potential Pn.

Thus, the presence or absence of the bond-dissociating particle model couple 21 can be accurately determined by the use of the molecular mechanics calculation which can reduce the computation time than the quantum mechanics calculation.

If it is determined in the step S47 that the bond-dissociating particle model couple/couples 21 exists/exist (in the step S47, "Y"es), the subsequent quantum mechanics calculation step S48 is performed, targeting on only the bond-dissociating particle model couple(s) 21.

If it is determined in the step S47 that there is no bond-dissociating particle model couple 21 (in the step S47, "N"o), the after-mentioned step S52 is performed.

Figure 13:
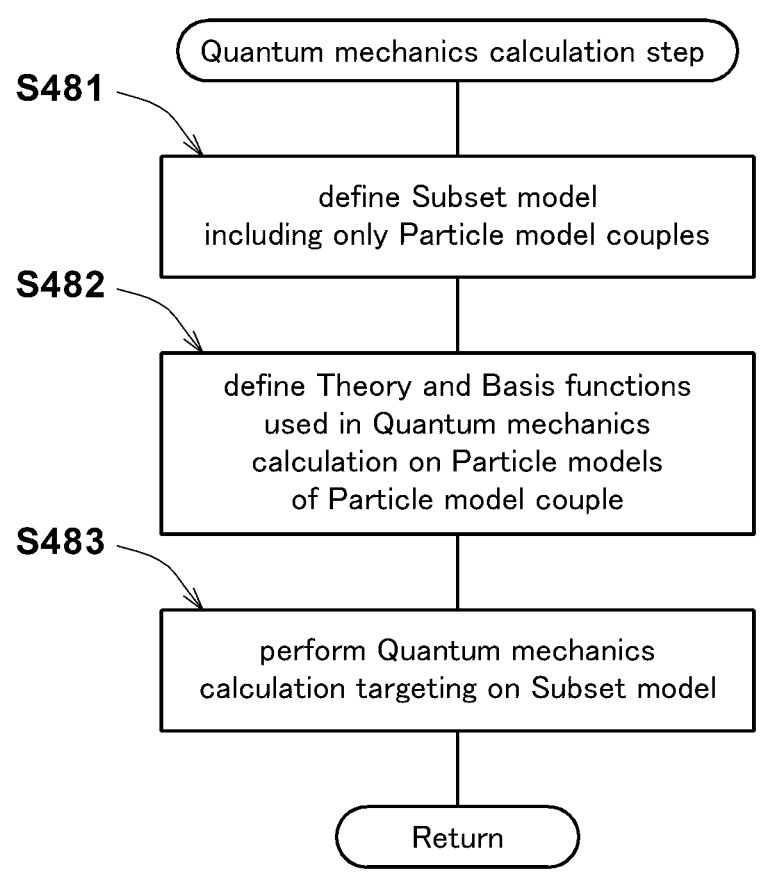
FIG. 13 shows a flow chart of an example of the quantum mechanics calculation step S48.

FIG. 13 shows a flow chart of the quantum mechanics calculation step S48.

In the step S48, the quantum mechanics calculation is performed on a subset model 22 including only the bond-dissociating particle model couple(s) 21.

In the quantum mechanics calculation step S48 in the present embodiment, first, a subset model 22 including only the bond-dissociating particle model couple(s) 21 is defined (step S481).

Figure 14:
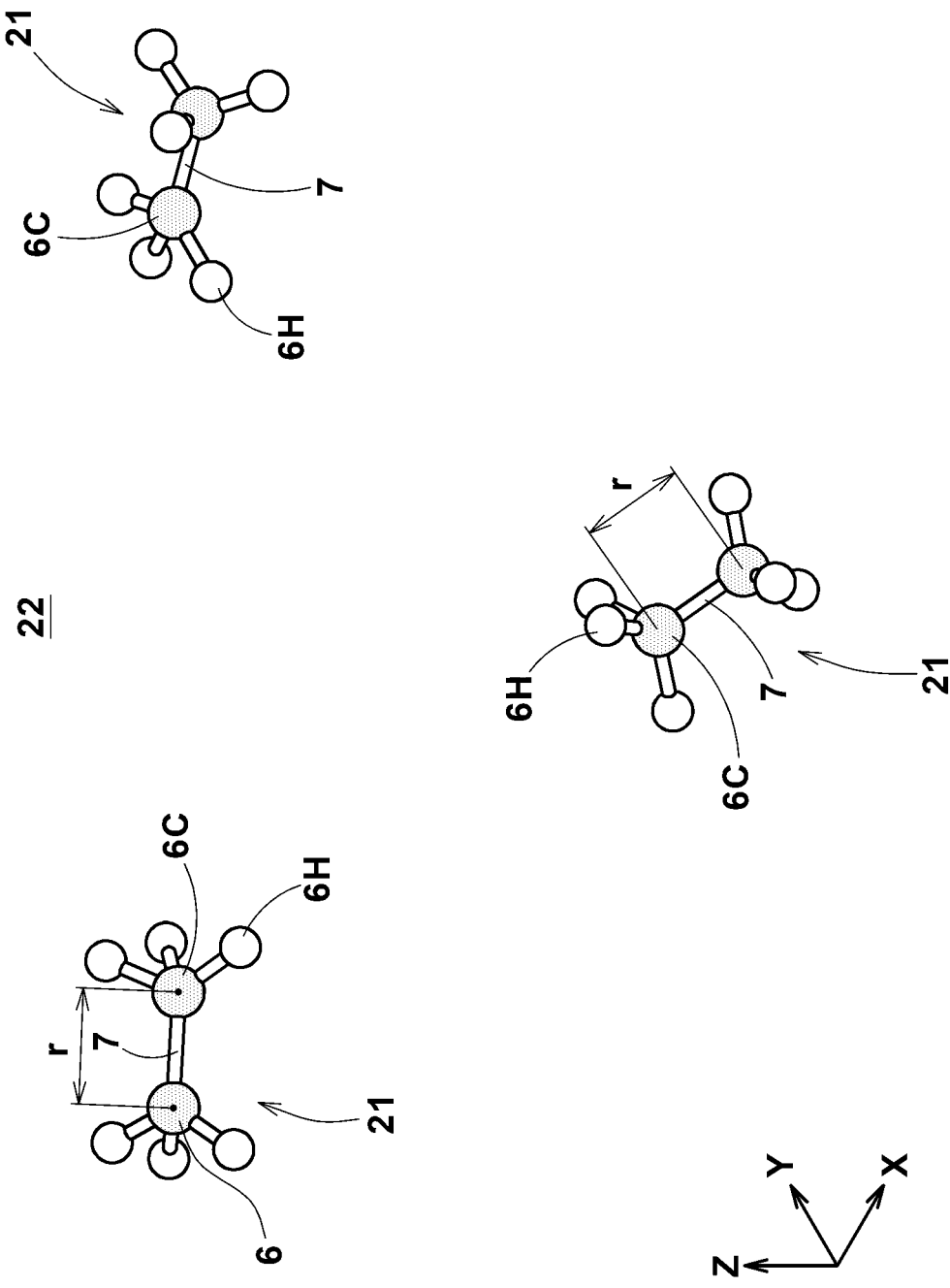
FIG. 14 shows a part of an example of the subset model.

FIG. 14 shows an example of the subset model 22.

The subset model 22 is a non-entire region constituted by only the bond-dissociating particle model couple(s) 21 existing in the molecular chain model(s) 5 of the polymeric material model 16. In other words, the subset model 22 is the same as the polymeric material model 16 except that the particle models and bond models other than the bond-dissociating particle model couple(s) 21 are eliminated from the molecular chain model(s) 5 in the polymeric material model 16.

Thus, if a plurality of bond-dissociating particle model couples 21 exist in the polymeric material model 16, all the particle model couples 21 are included in the subset model 22.

On the other hand, in each of the particle models 6 of the bond-dissociating particle model couple 21, if the difference N of the valency of the atom modeled by the particle model 6 minus the bond number of the particle model 6 is one or more, the number N of the hydrogen particle model(s) 6H is(are) bonded with the particle model 6 through the bond model(s) 7 in order to make the structure of the bond-dissociating particle model couple 21 stable during the quantum mechanics calculation.

In the quantum mechanics calculation step S48 in the present embodiment, the theory and basis functions used in the quantum mechanics calculation are defined on the particle models 6 of the bond-dissociating particle model couple 21 (step S482).

In the step S482, the bond potential Pn defined between the particle models 6 of the bond-dissociating particle model couple 21 is disabled, and the theory and basis functions used in the quantum mechanics calculation are defined instead.

The theory and basis functions used in the quantum mechanics calculation are described above.

Then, in the quantum mechanics calculation step S48 in the present embodiment, the quantum mechanics calculation is performed, targeting on the subset model 22, based on the Poisson's ratio set as the initial condition (step S483).

As described above, in the quantum mechanics calculation, as conforming to the interactions based on the nuclei and electrons, the electron state and motion of each particle model 6 are tracked every unit timestep of the simulation. Therefore, in the step S483, the elongation of the subset model 22 and the elongation of the bond-dissociating particle model couple 21 can be calculated with high accuracy as compared to the molecular mechanics calculation.

Further, in the step S483, as the quantum mechanics calculation is carried out targeting on the subset model 22 derived from the polymeric material model 16, the computation time is greatly reduced as compared with the case where the quantum mechanics calculation is performed targeting on the entirety of the polymeric material model 16.

In the step S483, the physical quantities including the energy Ec of the subset model 22 and a force Fc acting on the subset model 22 are calculated and stored in the computer 1.

Then, in the breaking calculation step S4 in the present embodiment, a molecular mechanics calculation is performed on the subset model 22 (Second molecular mechanics calculation step S49).

As explained above, the subset model 22 is a non-entire region constituted by only the bond-dissociating particle model couples 21 extracted from the molecular chain model 5 of the polymeric material model 16 deformed through the elongation step S45 as shown in FIG. 14.

In the second molecular mechanics calculation step S49, physical quantities including the energy Eb of the subset model 22 and a force Fb acting on the subset model 22 are calculated and stored in the computer 1.

Such physical quantities are utilized to determine the energy Et of the polymeric material model 16 and the force Ft acting on the polymeric material model 16 in accordance with the after-mentioned ONIOM method.

In the second molecular mechanics calculation step S49, the bond potential Pn is defined between the particle models 6 of the bond-dissociating particle model couple 21.

Then, in the breaking calculation step S4 in the present embodiment, the energy Et of the polymeric material model 16 is calculated and stored in the computer 1 (Step S50).

The energy Et is calculated by the following equation (6) based on the ONIOM (our own N-layered integrated molecular orbital and molecular mechanics) method.

$$Et = Ea - Eb + Ec \quad (6)$$

wherein
Ea: the energy of the polymeric material model obtained through the first molecular mechanics calculation step (S46),
Eb: the energy of the subset model obtained through the second molecular mechanics calculation step (S49), and
Ec: the energy of the subset model obtained through the quantum mechanics calculation step (S48).

The energy Ea of the whole of the polymeric material model 16 and the energy Eb of the subset model 22 obtained through the molecular mechanics calculations which are low in the calculation accuracy when compared to the quantum mechanics calculation. The energy Ec of the subset model 22 obtained through the quantum mechanics calculation is high in the calculation accuracy.

The ONIOM method can be said to be a method of obtaining an optimum solution by combining layers having different calculation accuracy. In the present embodiment, of the energy Ea of the polymeric material model 16, the energy Eb of the subset model is replaced by the energy Ec of the subset model, and thereby the energy Et of the polymeric material model 16 is obtained. In such energy Et, the effect of breakage of the molecular chain model 5 can be precisely included, therefore, the calculation accuracy can be improved.

Further, it is not necessary to perform the quantum mechanics calculation to accurately obtain the energy of the whole of the polymeric material model 16, therefore, it is possible to shorten the calculation time.

In the breaking calculation step S4 in the present embodiment, the force Ft acting on the polymeric material model 16 is calculated and stored in the computer 1 (step S51).

The force Ft is calculated by the following equation (7) based on the ONIOM method.

$$Ft = Fa - Fb + Fc \quad (7)$$

where,
Fa: the force acting on the polymeric material model obtained through the first molecular mechanics calculation step (S46),
Fb: the force acting on the subset model obtained through the second molecular mechanics calculation step (S49), and
Fc: the force acting on the subset model obtained through the quantum mechanics calculation step (S48).

In the present embodiment, of the force Fa acting on the polymeric material model 16, the force Fb obtained through the molecular mechanics calculation is replaced by the force Fc obtained through the quantum mechanics calculation. In such force Ft, the effect of breakage of the molecular chain model 5 can be precisely included, therefore, the calculation accuracy can be improved.

Further, it is not necessary to perform the quantum mechanics calculation to accurately obtain the force acting on the whole of the polymeric material model 16, therefore, it is possible to shorten the calculation time.

In the breaking calculation step S4 in the present embodiment, then, the coordinate values and velocity of each of the particle models 6 of the molecular chain model 5 are updated to the values at the current unit timestep (step S52).

In the present embodiment, the acceleration is calculated from the physical quantities including the energy Et and the force Ft calculated according to the above-mentioned ONIOM methods. Then, using the obtained acceleration, new coordinate values of each particle model 6 (i.e., the coordinate values to be used in the next unit timestep) are calculated from the previous coordinate values of each particle model 6 of the molecular chain model 5 before the first molecular mechanics calculation step S46 is performed.

The new or updated coordinate values of the particle models 6 include the coordinate values of the particle models 6 included in the subset model 22 and determined as being likely to bond-dissociate through the quantum mechanics calculation, therefore, it is possible to accurately analyze the breakage of the molecular chain models 5.

On the other hand, with respect to the portion of the molecular chain model less likely to bond-dissociate, the molecular mechanics calculations are performed, therefore, it is possible to shorten the calculation time.

In the first molecular mechanics calculation step S46 and the second molecular mechanics calculation step S49, as described above, the bond potential Pn approximating to the bond-dissociation potential Pu is defined.

Therefore, it is possible to minimize differences between forces acting on the particle models 6 after the second molecular mechanics calculation step S49 and forces acting on the particle models 6 after the quantum mechanics calculation step S48.

Thereby, it is possible to improve the calculation accuracy of the coordinate values obtained by the ONIOM method.

Further, the velocity of each particle model 6 is calculated based on the coordinate values of each particle model 6 of the molecular chain model 5, the energy Et of the polymeric material model 16 and the force Ft acting on the polymeric material model 16.

As described above, when it is determined in the step S47 that there is no bond-dissociating particle model couple 21 ("N"o in the step S47), the quantum mechanics calculation (step S48) and the molecular mechanics calculation (step S49) for the subset model 22 are not performed.

In this case, in the step S52, the coordinate values and the velocity are updated based on the coordinate values of the particle models 6 obtained through the molecular mechanics calculation targeting on the polymeric material model 16, the energy Ea obtained through the first molecular mechanics calculation step, and the force Fa obtained through the first molecular mechanics calculation step.

Then, in the breaking calculation step S4, for the subset model 22 after the quantum mechanics calculation step S48 (in the present embodiment, after the quantum mechanics calculation step S48 and the second molecular mechanics calculation step S49), it is judged whether the bond-dissociating particle model couple 21 whose distance r between the particle models 6 is larger than the predetermined second distance Lb exists or not (step S53).

In the step S53, based on the coordinate values of the particle models 6 of the molecular chain model 5 updated in the step S52, for each bond-dissociating particle model couple 21 existing in the subset model 22, the distance r between the particle models 6 is calculated.

The second distance Lb is a parameter for determining the occurrence of the bond-dissociation between the particle models 6 of the bond-dissociating particle model couple 21.

It is defined that the bond-dissociation occurs if the distance r is greater than the second distance Lb.

In the present embodiment, as shown in FIG. 12, the second distance Lb is larger than the first distance La and larger than the distance Ln between the particle models at the inflection point 13.

Figure 15A:
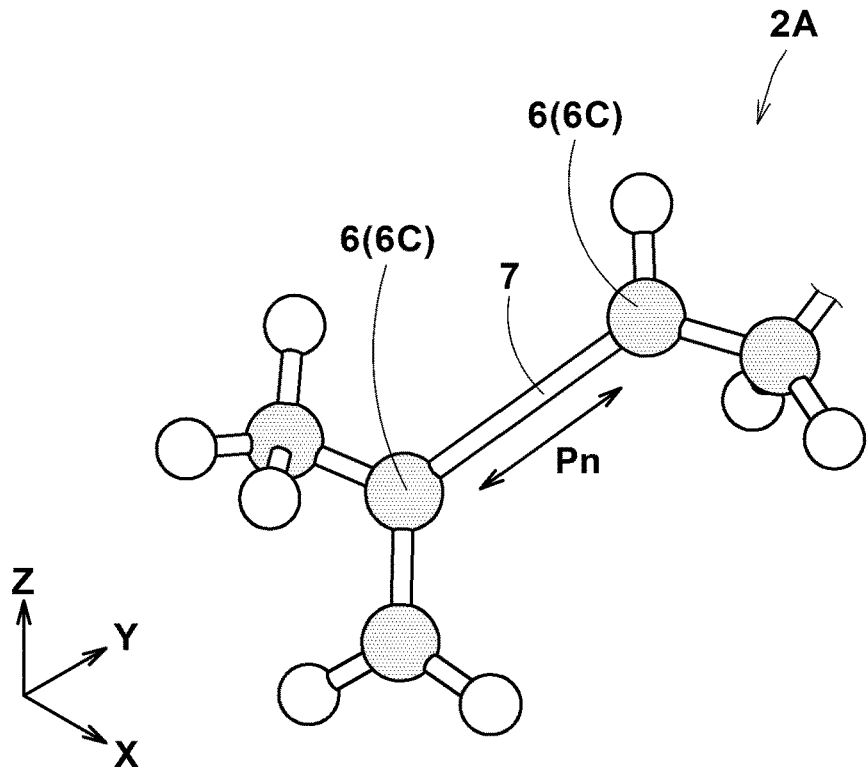
FIG. 15(*a*) is a diagram showing a part of the molecular chain model before the occurrence of the bond-dissociation between the particle models.
Figure 15B:
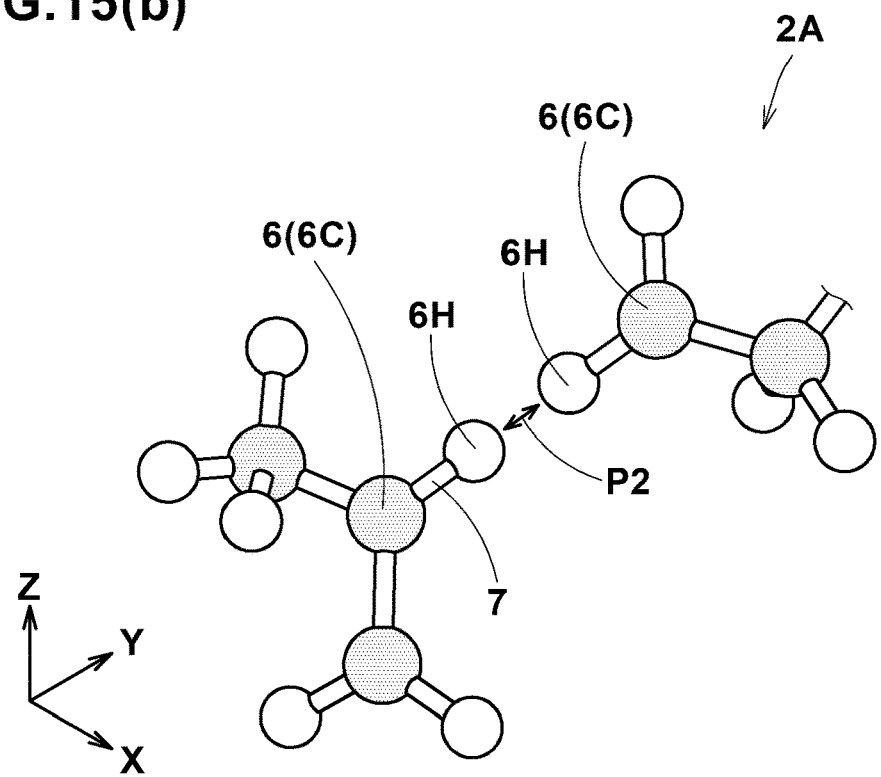

FIG. 15(*a*) is a diagram showing a part of the molecular chain model 5 before the occurrence of the bond-dissociation between the particle models 6.

FIG. 15(*b*) is a diagram showing the part of the molecular chain model 5 after the occurrence of the bond-dissociation between the particle models 6.

In the after-mentioned breaking step S54, of the particle models 6 in the molecular chain model 5, those corresponding to the bond-dissociating particle model couple(s) 21 in which the bond-dissociation is determined as being occurred, are uncoupled (bond-dissociated).

Such bond-dissociation is defined as follows:
the bond model 7 coupling between the concerned particle models 6 is disabled,
the bond potential Pn (shown in FIG. 15(*a*)) defined between the concerned particle models 6 is disabled, and
the second potential P2 (shown in FIG. 15(*b*)) is defined between the concerned particle models 6.

Further, the hydrogen particle models 6H are bonded with the uncoupled particle models 6 through the bond models 7. The number of the hydrogen particle models 6H is equal to the difference of the total valency of the atoms modeled by the uncoupled particle models 6 minus the total bond number of the uncoupled particle models 6. For example, if each of the uncoupled particle models 6 is carbon atom (valency=4) and the bond number is 3, then one hydrogen particle model 6H is bonded with the particle model 6 through a bond model 7.

On the other hand, as a result of defining such bond-dissociation condition, there is a possibility that the simulation calculation causes an abnormal end.

Therefore, the present inventors was studied and found that the difference between the energy of the subset model 22 obtained through the quantum mechanics calculation and the energy of the subset model 22 obtained through the molecular mechanics calculation increases as the distance between the particle models 6 decreases, and that, if the particle models 6 (e.g., carbon particle models 6C) are uncoupled without a sufficient distance therebetween, then the difference in the energy becomes increased in the uncoupled particle models 6, and the abnormal end tends to occur, and that, when the distance between the hydrogen particle models 6H newly coupled to the uncoupled particle models 6, respectively, becomes smaller than the equilibrium distance $r_0$, the repulsive force (12 squared term of the expression (4)) caused by the second potential P2 between the hydrogen particle models 6H is excessively increased, and as a result, the abnormal end is caused.

In the present embodiment, based on such findings, the second distance Lb is set to a value of the distance Ln between the particle models 6 at the inflection point 13 shown in FIG. 12, plus a value in a range from 1.0 to 2.5 angstroms.

Thus, in the after-mentioned breaking step S54, the particle models 6 are uncoupled after a sufficient distance is secured between the particle models 6, and as a result, after a sufficient distance is secured between the newly coupled hydrogen particle models 6H as shown in to FIG. 15(*b*).

Accordingly, an abnormal end of the calculation due to the increase in the difference in the energy can be prevented, and the breakage of the molecular chain model 5 can be calculated stably.

As to the second distance Lb, if the value added to the distance Ln at the inflection point 13 is less than 1.0 angstrom, there is a possibility that the difference in the energy can not be prevented from increasing. If greater than 2.5 angstroms, there is a possibility that the quantum mechanics calculation becomes unstable and likely to abend. Further, as the time until the particle model couples in the subset model 22 become uncoupled is increased, the computational load for the quantum mechanics calculation tends to increase.

From this point of view, the value in angstrom added to the distance Ln at the inflection point 13 is preferably 1.5 or more, and preferably 2.0 or less.

In the step S53, if the bond-dissociating particle model couple 21 whose distance r between the particle models 6 is the second distance Lb or more, exists ("Y"es in the step S53), then the breaking step S54 is carried out.

If does not exist ("N"o in the step S53), the aftermentioned step S55 of determining whether or not the polymeric material model 16 has been extended to a predetermined state, is performed.

In the breaking calculation step S4 in the present embodiment, then, the particle models 6 of the molecular chain model 5 corresponding to the bond-dissociating particle model couple 21 to be uncoupled are uncoupled (Breaking step S54). Such bond-dissociation is defined as has been described above. In the breaking step S54, the bond between the particle models 6 is dissociated based on the distance between the particle models 6 calculated from the coordinate values updated in the step S52. Such updated coordinate values are reflected by the coordinate values calculated by the quantum mechanics calculation, therefore, it is possible to accurately analyze the breakage of the molecular chain model 5.

As described above, in the simulation method in the present embodiment, the particle models 6 are bond-dissociated based on the results of the quantum mechanics calculation targeting on the subset model 22 including only the bond-dissociating particle model couple(s) 21, therefore, the breakage of the molecular chain model 5 can accurately simulate the breakage of the actual molecular chain. Thus, it is possible to accurately analyze the polymeric material.

As described above, in the step S47, the presence or absence of the bond-dissociating particle model couple(s) 21 is determined by the result of the molecular mechanics calculation whose computation time is shorter than the quantum mechanics calculation. Therefore, in the simulation method of the present embodiment, it is possible to shorten the computational time. Further, as the second distance Lb is set in the above range, it is possible to prevent the abnormal end of the computation, and the breakage of the molecular chain model 5 can be calculated stably.

In the breaking calculation step S4 in the present embodiment, whether or not the polymeric material model 16 is elongated to a predetermined state is determined (Step S55).

If the polymer material model 16 is determined in the step S55 as being elongated to an upper limit value ("Y"es in the step S55), the next step S5 is performed.

On the other hand, if the polymeric material model 16 is determined as being not elongated to the upper limit value ("N"o in the step S55), a unit timestep is incremented (Step S56), and then the step S45 to the step S55 are performed again.

Thus, in the breaking calculation step S4, it is possible to simulate the breakage of the molecular chain model 5 by elongating the polymeric material model to the upper limit.

In the simulation method in the present embodiment, next, as shown in FIG. 3, whether a physical quantity of the polymer material model 16 is within an allowable range or not is judged (step S5).

If the physical quantity of the polymeric material model 16 is determined in the step S5 as being within the allowable range ("Y"es in the step S5), then the polymer material is manufactured according to the polymeric material model 16 (step S6).

On the other hand, if the physical quantity of the polymer material model 16 is determined as being out of the allowable range ("N"o in the step S5), then conditions defined on the molecular chain model 5 are changed (step S7), and the step S1 to the step S5 are performed again.

Thus, in the present embodiment, until the physical quantity of the polymeric material model 16 becomes within the allowable range, the conditions of the molecular chain model 5 are changed, and the polymeric material having a desired performance, can be designed efficiently.

While detailed description has been made of an especially preferable embodiment of the present invention, the present invention can be embodied in various forms without being limited to the illustrated embodiment.

Comparison Test

According to the procedure shown in FIG. 3 and FIG. 5, the polymer models and molecular chain model were defined, and the breakage computing step of breaking the molecular chain model was performed (Embodiment examples an comparative examples).

In the breakage computing step of Embodiment examples and comparative examples, according to the procedure shown in FIGS. 8 and 13, the following steps were performed:

the step of performing the molecular mechanics calculation;
the step of performing the quantum mechanics calculation targeting on the subset model including only the bond-dissociating particle model couple whose distance between the particle models was larger than the first distance La; and
the step of performing the molecular mechanics calculation targeting on the subset model, and
according to the expressions (6) and (7),
the energy Et of the polymeric material model and the force Ft acting on the polymeric material model were calculated.

In the step of performing the molecular mechanics calculation of Embodiment examples and comparative examples, the bond potential approximating to the bond-dissociation potential was defined between the particle models of the molecular chain model.

Further, in the breaking step of Embodiment examples and comparative examples, when the distance between the particle models of the bond-dissociating particle model couple was greater than the second distance Lb, the bond between the particle models of the molecular chain model which particle models correspond those of the bond-dissociating particle model couple was dissociated.

The computation time until the polymeric material model reached to an upper limit (1100%) for the cell deformation (elongation), was measured.

In Embodiment examples Ex. 1-Ex. 4, the second distances Lb were set to values obtained by adding 1.0 to 2.5 angstroms to the distance between the particle models at the inflection point of the bond-dissociation potential.

In comparative example Ref. 1, the second distance was set to a value obtained by adding 0.5 angstrom to the distance between the particle models at the inflection point of the bond-dissociation potential.

In comparative example Ref. 2, the second distance was set to a value obtained by adding 3.0 angstroms to the distance between the particle models at the inflection point of the bond-dissociation potential.

The potentials defined between the particle models and the software used were as described above.

Common specifications are as follows.

Computer: SGI's workstation (CPU: 12 cores, memory: 64 GB)

Polymer model:
 Length of each side of cell: 2.3 nm
 Number of Molecular chain model in cell: one Molecular chain model:
  Number of particle models (atoms): 1301
  Polyisoprene (Isoprene molecular: 100 monomers) cross-linked by sulfur (1 atom)
 Distance Ln at Inflection point: 3.09 angstroms
 First distance La: 2.69 angstroms Elongation simulation:
 Elongating direction: one axis direction (z-axis direction)
 Elongation rate Va: 250 meters/sec
 Upper limit for cell deformation: 1,100%
 Test results are shown in Table 1.

As shown, in the Embodiment examples Ex. 1-Ex. 4, the polymeric material model could be elongated up to 1100% without the abnormal end of the computation.

In the comparative examples Ref. 1 and Ref. 2, the abnormal end occurred at the elongation of 700%.

As compared to the Embodiment examples Ex. 1 and Ex. 2, the Embodiment examples Ex. 2 and Ex. 3 whose second distance Lb was added by 1.0 to 2.0 angstroms were remarkably decreased about 1800 hours (75 days) in the computation time without sacrificing the calculation accuracy.

TABLE 1

| | Ref.1 | Ex.1 | Ex.2 | Ex.3 | Ex.4 | Ref.2 |
|---|---|---|---|---|---|---|
| Second distance Lb *1 | +0.5 | +1.0 | +1.5 | +2.0 | +2.5 | +3.0 |
| computation time (hour) | abend | 2420 | 2650 | 3060 | 4260 | abend |

*1) value in angstrom added to the distance at the inflection point

The invention claimed is:

1. A simulation method for analyzing a breakage of a molecular chain of a polymer material using a computer, comprising:
 a step of defining in the computer a molecular chain model of the molecular chain comprising particle models and bond models bonding between the particle models,
 a step of defining in the computer a cell which is a virtual space corresponding to a portion of the polymeric material,
 a step of defining a polymeric material model by setting at least one molecular chain model in the cell,
 a breaking calculation step of calculating a breaking of the molecular chain model with the computer based on a predetermined condition,
 wherein the breaking calculation step comprises:
  a step of defining molecular models each comprising a pair of particle models and a bond model bonding therebetween which are selected from the molecular chain model,
  a step of obtaining a bond-dissociation potential by performing a quantum mechanics calculation using the molecular models and obtaining an inflection point of the bond-dissociation potential at which an energy increment becomes smaller,
  a first molecular mechanics calculation step of performing a molecular mechanics calculation using the polymeric material model,
  a step of determining whether or not a particle model couple exists in the molecular chain model after the first molecular mechanics calculation step, the particle model couple being a pair of the particle models bonded through the bond model whose distance is greater than a predetermined first distance,
  a quantum mechanics calculation step in which, if the particle model couple exists, a quantum mechanics calculation is performed targeting on a subset model including only the particle model couple or couples, and
  a breaking step of dissociating the bond between the particle models in the molecular chain model which particle models correspond to each said particle model couple, if the distance between the particle models in the subset model after the quantum mechanics calculation step, is larger than a second distance, the second distance being larger than the first distance and equal to a distance between the particle models at the inflection point plus a value of from 1.0 to 2.5 angstrom, and
 wherein the first distance is smaller than a distance between the particle models at the inflection point.

2. The simulation method according to claim 1, wherein the breaking calculation step further comprises a second molecular mechanics calculation step of performing a molecular mechanics calculation targeting on only the subset model.

3. The simulation method according to claim 2, wherein the breaking calculation step further comprises
 a step of calculating physical quantities including an energy Et of the polymeric material model and a force Ft acting on the polymeric material model based on calculation results of the first molecular mechanics calculation step, the second molecular mechanics calculation step and the quantum mechanics calculation step, and
 a step of updating coordinates of the particle models based on the physical quantities, and
 in the breaking step, based on the distance between the particle models calculated from the coordinate values, the bond between the particle models is dissociated.

4. The simulation method according to claim 3, wherein the energy Et is calculated by the following expression Et=Ea−Eb+Ec, wherein
 Ea: an energy of the polymeric material model obtained through the first molecular mechanics calculation step,
 Eb: an energy of the subset model obtained through the second molecular mechanics calculation step, and
 Ec: an energy of the subset model obtained through the quantum mechanics calculation step.

5. The simulation method according to claim 3, wherein the force Ft is calculated by the following expression Ft=Fa−Fb+Fc, wherein Fa: a force acting on the polymeric material model obtained through the first molecular mechanics calculation step, Fb: a force acting on the subset model obtained through the second molecular mechanics calculation step, and Fc: a force acting on the subset model obtained through the quantum mechanics calculation step.

6. A method of manufacturing a polymer, comprising the step of using the simulation method according to claim 1.

* * * * *